(12) United States Patent
Gazeley et al.

(10) Patent No.: US 10,675,418 B2
(45) Date of Patent: Jun. 9, 2020

(54) DRUG DELIVERY DEVICE WITH LOAD INDICATOR

(71) Applicant: SANOFI, Paris (FR)

(72) Inventors: Oliver Charles Gazeley, Leamington Spa (GB); James Lewis Gareth, High Wycombe (GB); Daniel Thomas De Sausmarez Lintell, Rugby (GB); Matthew Meredith Jones, Warwick (GB); Robert Frederick Veasey, Leamington Spa (GB); David Plumptre, Droitwich Spa (GB); Anthony Paul Morris, West Midlands (GB)

(73) Assignee: Sanofi, Paris (FR)

( * ) Notice: Subject to any disclaimer, the term of this patent is extended or adjusted under 35 U.S.C. 154(b) by 84 days.

(21) Appl. No.: 15/742,555

(22) PCT Filed: Jul. 7, 2016

(86) PCT No.: PCT/EP2016/066198
§ 371 (c)(1),
(2) Date: Jan. 8, 2018

(87) PCT Pub. No.: WO2017/005878
PCT Pub. Date: Jan. 12, 2017

(65) Prior Publication Data
US 2018/0200457 A1 Jul. 19, 2018

(30) Foreign Application Priority Data
Jul. 8, 2015 (EP) .................................... 15306121

(51) Int. Cl.
*A61M 5/48* (2006.01)
*A61M 5/20* (2006.01)
(Continued)

(52) U.S. Cl.
CPC .............. *A61M 5/486* (2013.01); *A61M 5/20* (2013.01); *A61M 5/31515* (2013.01);
(Continued)

(58) Field of Classification Search
CPC ...... A61M 2205/581; A61M 2205/582; A61M 2205/583; A61M 2205/584;
(Continued)

(56) References Cited

U.S. PATENT DOCUMENTS 4,064,879 A * 12/1977 Leibinsohn ........... A61M 5/486
604/121
5,947,935 A * 9/1999 Rhinehart ......... A61M 5/14546
604/131
(Continued)

FOREIGN PATENT DOCUMENTS

CN 1665562 9/2005
CN 104093438 10/2014
(Continued)

OTHER PUBLICATIONS

International Preliminary Report on Patentability in International Application No. PCT/EP2016/066198, dated Jan. 9, 2018, 6 pages.
(Continued)

*Primary Examiner* — Quynh-Nhu H. Vu
(74) *Attorney, Agent, or Firm* — Fish & Richardson P.C.

(57) ABSTRACT

A drug delivery device includes a piston rod which extends along a longitudinal axis of the drug delivery device, wherein the piston rod is adapted to apply an axial load in the distal direction to a cartridge bung in order to dispense a medicament contained in the cartridge. In order to improve the convenience of the injection process and to mitigate the risk of underdosing due to a blocked needle a cartridge bung load indicator is provided, located at the distal end of the piston rod and adapted to abut against the cartridge bung, wherein the cartridge bung load indicator comprises an indicator element that audibly, tangibly and/or visually indicates a load state of the piston rod to the user.

8 Claims, 7 Drawing Sheets

(51) Int. Cl.
*A61M 5/50* (2006.01)
*A61M 5/315* (2006.01)
*A61M 5/168* (2006.01)
*A61M 5/31* (2006.01)

(52) U.S. Cl.
CPC . *A61M 5/5086* (2013.01); *A61M 2005/16863* (2013.01); *A61M 2005/3125* (2013.01); *A61M 2205/332* (2013.01); *A61M 2205/52* (2013.01); *A61M 2205/581* (2013.01); *A61M 2205/582* (2013.01); *A61M 2205/583* (2013.01); *A61M 2205/587* (2013.01)

(58) Field of Classification Search
CPC .. A61M 2205/587; A61M 5/20; A61M 5/315; A61M 2005/31508; A61M 2005/3151; A61M 5/31513; A61M 5/31515; A61M 5/486; A61M 5/5086
See application file for complete search history.

(56) References Cited

U.S. PATENT DOCUMENTS

| | | | |
|---|---|---|---|
| 6,565,531 B1* | 5/2003 | Mori | A61M 5/1454 604/135 |
| 2003/0233075 A1 | 12/2003 | Huegli | |
| 2012/0209111 A1 | 8/2012 | Cowan et al. | |
| 2015/0080790 A1* | 3/2015 | Munk | A61M 5/14566 604/67 |
| 2015/0088092 A1* | 3/2015 | Holm | A61M 5/16831 604/506 |
| 2015/0190581 A1* | 7/2015 | Jugl | A61M 5/31513 604/228 |
| 2015/0198248 A1* | 7/2015 | Kiilerich | F16J 1/005 92/172 |
| 2015/0320934 A1* | 11/2015 | Draper | G01D 5/32 604/154 |

FOREIGN PATENT DOCUMENTS

| | | |
|---|---|---|
| CN | 104271043 | 1/2015 |
| CN | 104755118 | 7/2015 |
| WO | WO 03/101527 | 12/2003 |
| WO | WO 2010/139641 | 12/2010 |
| WO | WO 2011/090427 | 7/2011 |
| WO | WO 2014/067879 | 5/2014 |
| WO | WO 2014/118107 | 8/2014 |
| WO | WO 2014/128157 | 8/2014 |

OTHER PUBLICATIONS

International Search Report and Written Opinion in International Application No. PCT/EP2016/066198, dated Sep. 21, 2016, 9 pages.

* cited by examiner

DRUG DELIVERY DEVICE WITH LOAD INDICATOR

CROSS REFERENCE TO RELATED APPLICATIONS

The present application is the national stage entry of International Patent Application No. PCT/EP2016/066198, filed on Jul. 7, 2016, and claims priority to Application No. EP 15306121.3, filed in on Jul. 8, 2015, the disclosures of which are expressly incorporated herein in entirety by reference thereto.

TECHNICAL FIELD

The present disclosure is generally directed to a drug delivery device, i.e. a handheld injection device for selecting and dispensing a dose of a medicament.

BACKGROUND

Drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a dose of a medicament, which may be a fixed dose or a user-variable dose. The medicament is usually contained within a cartridge. There are basically two types of drug delivery devices: resettable devices (i.e., reusable) and non-resettable (i.e., disposable). For example, disposable drug delivery devices are supplied as self-contained devices. Such self-contained devices contain pre-filled cartridges which may not be removed from these devices and replaced without destroying the device itself. In contrast, the reusable devices comprise a mechanism with which an empty or nearly empty cartridge may be replaced by a full cartridge. Consequently, such disposable devices need to have a resettable dose setting mechanism. The present disclosure is in general applicable for both types of devices, i.e. for disposable devices as well as for reusable devices.

In order to dispense the medicament from the cartridge the drug delivery device usually comprises a dose mechanism which drives a bung (piston) of the cartridge in the distal direction forcing the medicament contained in the cartridge out of a needle which is connected with a distal opening of the cartridge. In particular, the load provided by the dose mechanism to the bung is transmitted by a rod-like driving element (drive train), in the following referred to as piston rod. The piston rod is axially displaceable and applies a load in the distal direction along or parallel to the longitudinal axis of the drug delivery device to the cartridge bung, wherein the load is generated by the dose mechanism.

SUMMARY

Document WO 2014/128157 A1 discloses a drug delivery device with drug expelling means comprising dose setting means allowing a user to set a dose of drug to be expelled, an axially displaceable piston rod adapted to move the piston of a cartridge in the distal direction to thereby expel drug from the cartridge and a rotational member adapted to rotate relative to the housing corresponding to a set and/or expelled dose. Further, a sensor means is provided which is adapted to detect a set and/or an expelled dose. The known device additionally comprises a logging module which is provided with an axial switch allowing the module to detect whether the mechanism is in the setting or expelling mode. Therefore, the logging module realizes three different states depending on its distal position in which an axial switch lateral projection is positioned in the corresponding housing opening and rotationally locked to the housing via a rotary sensor holder. In the initial proximal position the switch projection engages a proximal edge of the opening and a flexible switch arm with a contact point is thereby held out of contact with a first rotary sensor part, in an intermediate position the switch projection still engages the proximal edge of the opening, however, the logging module has been moved distally and thereby the first rotary sensor part has been moved into contact with the switch arm, this bringing the axial switch into an "on" state detectable by a logging module circuitry. In an actuated distal position the switch projection has been moved out of engagement with the proximal edge of the opening, the axial switch thus remaining in its "on" state ensuring that the expelling mode is safely registered by the axial switch before the dosing mechanism is actually released.

Document WO 2010/139641 A1 refers to a drug delivery device containing a spindle used to expel a medicament from a container. The known drug delivery device comprises a rotatable spindle (piston rod) having a distal end and a disc-shaped bearing attached to the distal end of the spindle through a first connection comprising a web that fixedly attaches the bearing to the spindle to prevent independent movement of the bearing relative to the spindle. The first connection changes to a second connection which is created when the web is severed and disconnected from the bearing. This takes place before a first dose of medicament is delivered to the user, preferably during assembly of the device before it leaves the factory.

With current pen injectors patients are typically instructed to hold the dose button down for 10 seconds after completion of the injection stoke in order to ensure that the full dose of medicament is delivered. This is because there is typically some compliance within the dose delivery system (and the cartridge assembly in particular) so that the pressure build up during dispense causes deflection of this system. At the end of the injection stroke the remainder of the dose fluid is dispensed from the needle to complete the dose and relieve the pressure within the system. The exact time period required for this to happen depends on a number of factors, including: speed of injection stroke, cannula size (inner bore diameter) and viscosity of the medicament being delivered. For pen-injectors of the type used for the delivery of insulin a 10-second-dwell-period is typically recommended in the instructions provided to patients/users. This period is generally considered sufficient duration for the vast majority of users and use cases, even though it is likely to be potentially excessive for a reasonable proportion of users. Anecdotally, it is likely that many patients either ignore this step, or do not wait for the full 10 second period. Doing so they are at risk of receiving a partial under-dose.

There is an industry trend toward the use of smaller and smaller gauge cannula in the type of needle typically used for self injection. While small gauge cannula typically reduce the pain associated with the procedure, their use can result in an increased prevalence of some user/user-related risks. One particular risk associated with small gauge needles is an increased risk of partial or complete occlusion of the cannula.

Typically, users are instructed to undertake at least one prime dose before administering an injection and not to re-use needles, however it is widely known that such instructions are not always adhered to. If drug delivery is attempted with a blocked or missing needle then the delivery device is typically designed to stall under the applied load (rather than fail in an uncontrolled manner). However, compliance in the cartridge and drive mechanism often means that it is possible for the delivery mechanism (and associated dose indication means) to advance by an amount before becoming jammed. For injection devices where there is a direct mechanical connection between the force input interface (e. g. dose delivery button) and the proximal face of the bung in the medicament cartridge, for relatively large doses the user may be able to detect the increase in the reaction load at the force input interface, and also the fact that the button has not returned to its rest position. However, for devices such as auto-injectors, where there is no direct mechanical connection between the force input interface (e. g. dose delivery button) and the proximal face of the bung in the medicament cartridge, this feedback mechanism does not exist and so the user may be unaware that they have received a partial underdose or (for doses that are comparable in size to the compliance within the system) no dose. For such devices, the provision of dose completion feedback based on the presence or absence of residual pressure within the cartridge, rather than on mechanical displacement alone, might provide a useful mitigation measure to address the risks posed by a blocked needle event.

In addition, users of existing known injection devices are typically advised to keep the needle in their skin for a short period of time after the end of the dispensing action (10 seconds is common). This is required to provide sufficient time for fluid to be dispensed, releasing residual pressure in the cartridge allowing any compliant components in the system to return to their pre-dose state.

Certain aspects of the present disclosure can be implemented to provide a drug delivery device which improves the convenience of the injection process and mitigates the risk of under dosing due to a blocked needle.

The above problem is solved by a cartridge bung load indicator that is located at the distal end of the piston rod and adapted to abut against a cartridge bung, wherein the cartridge bung load indicator comprises an indicator element that audibly, tangibly and/or visually indicates a load state of the piston rod to the user.

According to the disclosure the load state is a state in which the axial load of the piston rod applied to the cartridge bung in the distal direction is equal to or exceeds a predefined minimum load value. This minimum load value may be defined for each type of drug delivery device separately. In contrast, the unload state refers to a situation in which the axial load of the piston rod applied to the cartridge bung in the distal direction is lower than the respective predefined minimum load value.

The disclosure focuses on using the relative fluid pressure in the cartridge to determine the dosing state or a blocked needle condition (e.g. elevated pressure indicating that the system is attempting to deliver the dose). During a dose event the drive system (dose mechanism) typically generates an axial force that is applied to the proximal face of the bung in the drug cartridge. This force is applied to the fluid contained there-in which acts to drive it out of the needle. Due to the restriction provided by the needle, a back pressure is generated in the cartridge which in turn creates a reaction load on the piston rod. According to the disclosure, the reaction load during dosing is used to activate a 'flag' or indicator element which visually, audibly and/or tangibly indicates that dosing is being attempted/underway or visually, audibly and/or tangibly indicates whether the needle is blocked and the pressure in the cartridge cannot be relieved. The functionality is achieved according to the disclosure by replacing a bearing component typically found in pen-injectors with a surprisingly low-cost and simple compliant sub-assembly, namely the cartridge bung load indicator, comprising the indicator element. The embodiments of the disclosure described in the following provide the indication of the load state by either mechanical or electronic means.

In a preferred embodiment the cartridge bung load indicator comprises a resiliently compressible housing which decreases in its length in the axial direction in response to an applied axial load. This is realized by a first, preferably sleeve-like casing element and a second, preferably sleeve-like casing element which are in (in the axial direction) slidable engagement with each other. Further, the first casing element is biased against the second casing element, for example by a pressure coil spring or wave spring so that the initial length in the axial direction is resumed when the axial load decreases.

In another embodiment the indicator element comprises at least one colored and/or patterned surface element, for example at a pin (nose, land, up-stand feature), which is unmasked in the load state. This embodiment refers to a simple and cost-effective mechanical cartridge bung load indicator. In the load state the colored or patterned pin is unmasked and thereby visible to the user. If the piston rod is not in the load state, that means that the axial load of the piston rod is lower than the predefined minimum load value (unload state), the pin is masked. Preferably, the pin is attached to the second casing element and covered by the first and/or second casing element if the piston rod is not in the load state. Unmasking in the load state is preferably realized by protrusion of the at least one pin from the first casing element, for example through an aperture in the first casing element. Alternatively or additionally, the colored and/or patterned element may be provided at another location, for example at the outer surface of the side wall of first casing element. In the unloaded state, the colored and/or patterned element is covered/masked by the respective other casing element, e.g. the second casing element and in the loaded state it is visible in an aperture of the respective other casing element, e.g. the second casing element. Naturally, the colored and/or patterned element may be provided at the outer surface of the side wall of the second casing element.

In a further embodiment the indicator element comprises a lighting element and/or display that lights up and/or flashes and/or shows a warning message in the load state. With such electronic indicator element the load state may be more perceptible for the user who may suffer from impaired vision. Further, different colors, flash modes or warning messages may be realized, for example the warning message or color may be changed after a pre-determined period of time after activation, for example when the system is unable to complete the delivery of a dose, e. g. due to a blocked needle. Preferably, the lighting element and/or display comprise at least one LED, preferably a plurality of LEDs with different colors, or an LCD.

Additionally or alternatively, the indicator element may comprise a sound element that produces an audible sound in the load state. A sound indication may be even more perceptible for the user, in particular for a user that suffers from impaired vision.

Further additionally or alternatively, the indicator element comprises a vibrating or rocking module that vibrates the device in the load state in order to tangibly indicate the load state to the user. This indicator element type has the same advantages as the sound element.

In another embodiment the cartridge bung load indicator is attached to the piston rod by a connection which allows relative movement of the piston rod and the cartridge bung load indicator in the axial direction, wherein the relative movement is limited to a predefined distance. This balances load fluctuations and differentiates inadvertent small movement of the piston rod from the "real" dispensing movement. In one embodiment, the connection between the piston rod and the cartridge bung load indicator may be releasable, which may be advantageous for reusable drug delivery devices.

In another embodiment the cartridge bung load indicator comprises a memory storing data regarding the load state of the piston rod.

In another embodiment the drug delivery device comprises a cartridge containing a medicament and a bung (piston) located at the proximal end of the cartridge. In the fully assembled state (for example also after cartridge replacement) the cartridge bung load indicator abuts the bung of the cartridge. Preferably, the cartridge is fixed to the drug delivery device by means of a cartridge holder.

It is further preferred if the lighting element and/or display is accommodated such that it illuminates the cartridge and/or the cartridge holder. Therefore, a series of LEDs (or similar lighting elements) may be located circumferentially at the proximal end of the cartridge or a cartridge holder component. Utilizing the phenomenon of total internal reflection, the light emitted by the LED will make the cartridge and/or cartridge holder appear to light up until the LEDs are turned off. By utilizing different colors and/or flashing a high sophisticated realization of a visual indication of the state of the system (dispense operation in progress or dose delivery completed) to the user is achieved.

The above disclosure may be used within a pen type injector for the delivery of medicament into the body by means of a needle. The disclosure is suitable for disposable or reusable devices as well as for devices administering user-settable doses or pre-defined (non user-settable) doses.

The cartridge of the drug delivery device typically contains a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM. The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

The present disclosure will now be described in further detail with reference to the accompanying schematic drawings, in which.

DETAILED DESCRIPTION

Figure 1:
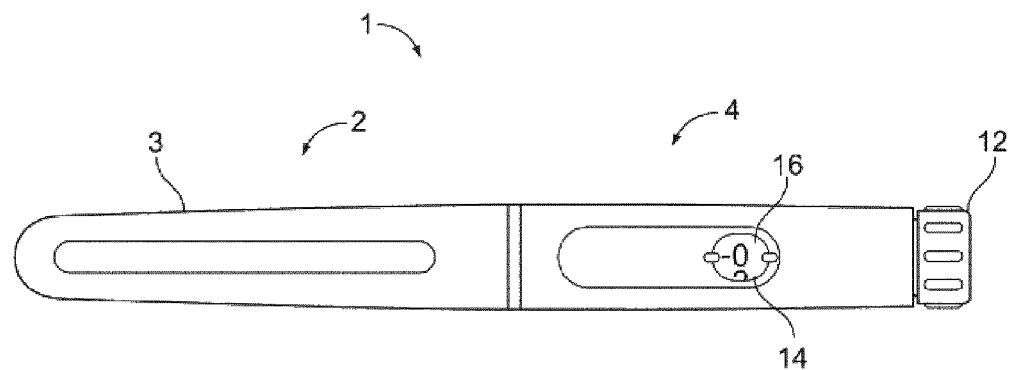
FIG. 1 shows a first embodiment of the inventive drug delivery device in a side view with cap.
Figure 2:
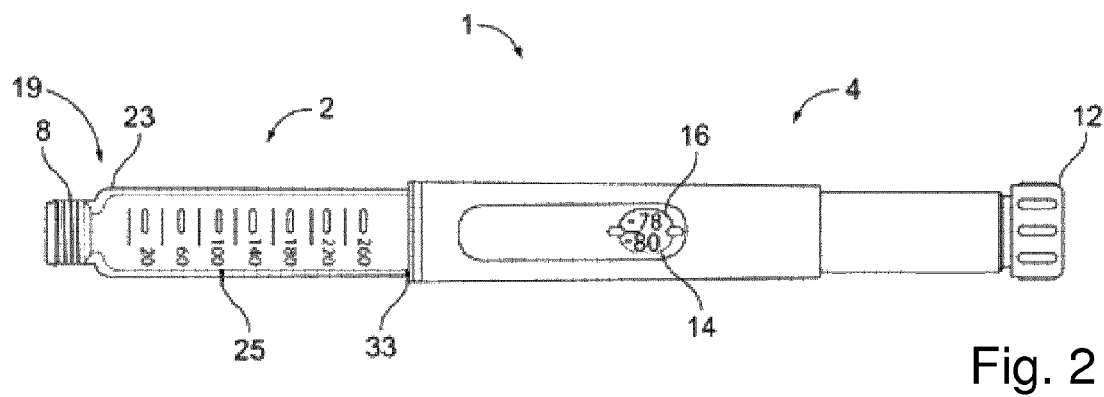
FIG. 2 illustrates the inventive drug delivery device of FIG. 1 with cap removed in a side view.

Referring to FIGS. 1 and 2 there is shown a drug delivery device in accordance with an exemplary arrangement. The drug delivery device 1 comprises a housing having a cartridge retaining part 2 and a dosing mechanism 4. The drug delivery device may be a resettable drug delivery device (i.e. a reusable device) or alternatively a non-resettable drug delivery device (i.e. a non-reusable device). A first end of the cartridge retaining part 2 and a second end of the dose setting mechanism 4 are secured together by connecting features. For non-resettable devices these connecting features would be permanent or non-reversible. For reversible devices these connecting features would be releasable. The dosing mechanism 4 is adapted to select a user settable dose and to drive a piston rod 6 (see FIG. 3) during dose dispense into the distal direction.

A removable cap 3 is releasably retained over the distal end 19 of the cartridge retaining part 2. The dosing mechanism 4 comprises a dial grip 12 and a window or lens 14. A dose scale arrangement 16 is viewable through the window or lens 14. To set a dose of a medicament contained within the drug delivery device, the user rotates the dose dial grip 12 such that the dialed dose will become viewable in the window or lens 14 by way of the dose scale arrangement 16. For dose dispense the user may push a dose button 17 into the distal direction. Such activation of the dose button 17 causes the dosing mechanism to apply a load to the piston rod 6 and to move it into the distal direction. Further details regarding dose setting and dose dispensing with the drug delivery device are described in patent application No. EP 14 306 064.8, the content of which is included herein by reference.

After removal of the cap 3 from the distal end 19 of the drug delivery device 1 the cartridge holder 23 is exposed. As illustrated the cartridge 25 is fixed within the cartridge holder 23 and contains a type of medicament that can be administered relatively often such as once or more times a day. At the distal end of the cartridge holder 23 a thread 8 is provided for attachment of a needle component comprising a needle (not shown). The cartridge further comprises a bung, piston or stopper 27 (see FIG. 3) that is retained near or at a proximal end 33 of the cartridge 25 before the first dose is administered. For dose dispense the bung 27 is movable in the distal direction within the cartridge 25.

Figure 3:
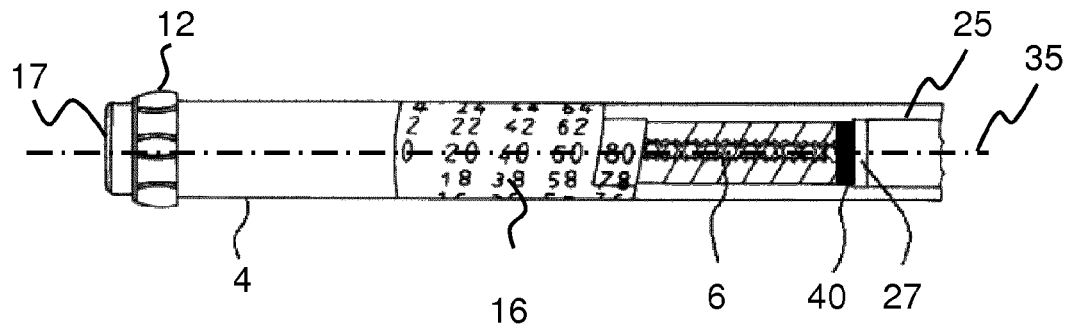
FIG. 3 shows an inner portion of the drug delivery device of FIG. 1 in a side view.

As in principle shown in FIG. 3 the piston rod running along the longitudinal axis 35 of the device 1 is connected to a cartridge bung load indicator 40 wherein the cartridge bung load indicator 40 abuts the bung 27 of the cartridge 25 for transmitting a load from the dosing mechanism 4 to the bung 27 during dose dispense. Different embodiments of the inventive cartridge bung load indicator 40 are explained in detail below.

Figure 4:
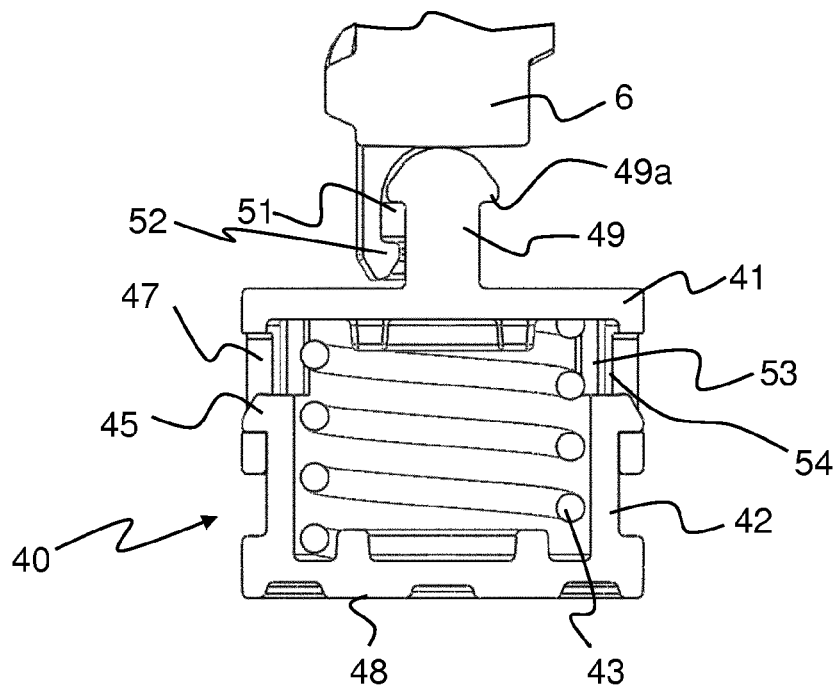
FIG. 4 depicts a cross section of a first embodiment of a cartridge bung load indicator according to the disclosure.

As illustrated in FIG. 4 a first embodiment the cartridge bung load indicator 40 comprises two casing components, namely a sleeve-like or can-like first casing element 41 and a sleeve-like or can-like second casing element 42, as well as a coil spring 43 in the form of a compression spring. The coil spring 43 is accommodated within the first casing element 41 and the second casing element 42 such that it drives both parts apart from each other.

At the proximal end of the second casing element 42 the cartridge bung load indicator 40 provides at least one radial protrusion 45 which is movable within a respective groove or slit 47 within the shell wall of the first casing element 41 wherein the axial length of the groove 47 determines the axial movement of the first casing element 41 relative to the second casing element and change of the overall length of the cartridge bung load indicator 40 in the axial direction.

The second casing element 42 forms an outer end face 48 (see FIG. 4) at its distal end which is adapted to abut the bung 27 of the cartridge 25 as shown in FIG. 3.

The first casing element 41 comprises at its proximal end an axially protruding stud 49 forming a mushroom-like head 49a at its proximal end. The head 49 of the stud 49 is accommodated within a respective groove 51 at the distal end of the piston rod 6 forming a snap-fit connection between the cartridge bung load indicator 40 and the piston rod 6. The form of the groove 51 and the head 49 allows limited movement of the cartridge bung load indicator 40 and the piston rod 5 relative to each other in the axial direction. The limitation of the movement is provided by a radially protruding rib 52 at the groove 51 of the piston rod 6 and the radial projection of the head 49a.

Figure 6:
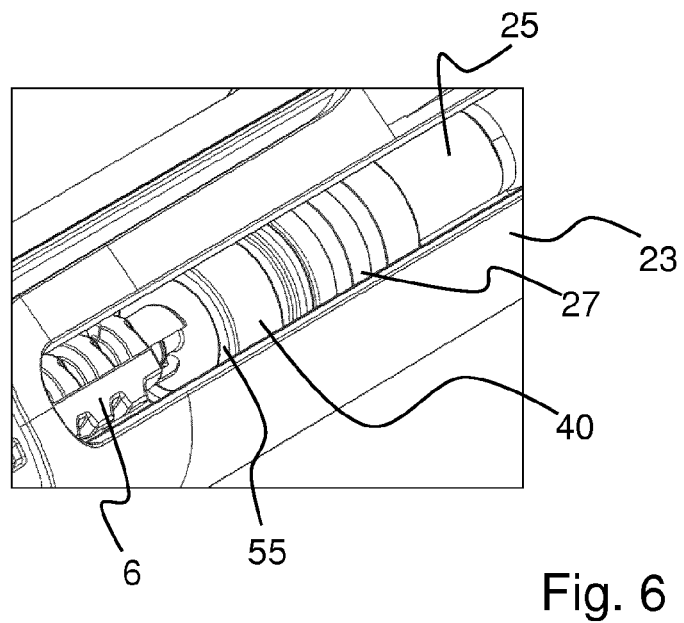
FIG. 6 depicts a second embodiment of the inventive drug delivery device with a cartridge bung load indicator according to FIG. 4 not in the overload state in a perspective view from the side.
Figure 7:
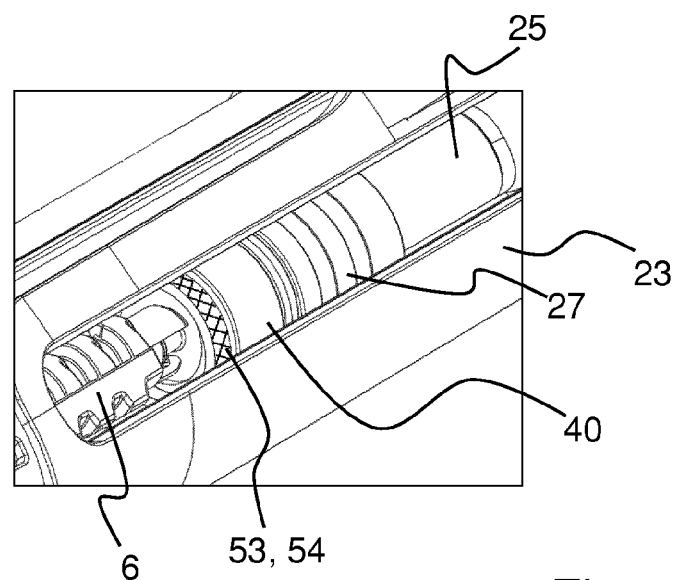
FIG. 7 depicts the drug delivery device of FIG. 6 in an overload state in a perspective view from the side.
Figure 8:
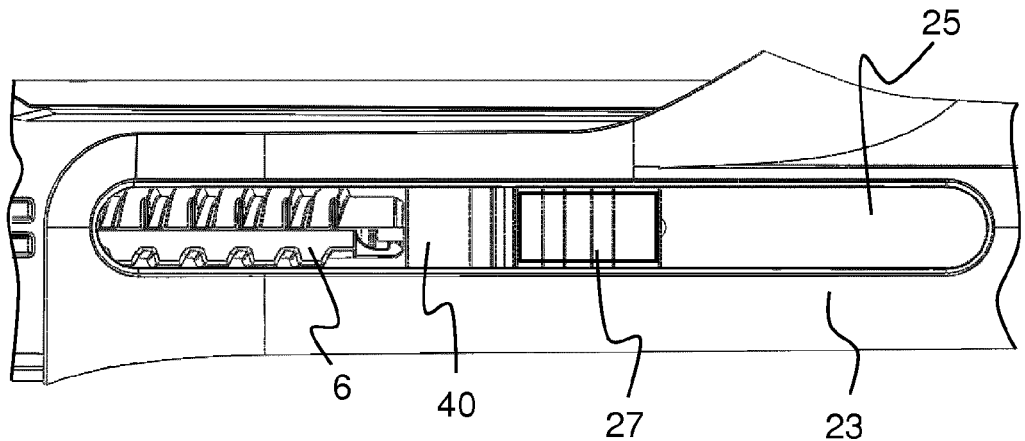
FIG. 8 shows a portion of the drug delivery device of FIG. 6 prior to medicament dispense in a side view.
Figure 9:
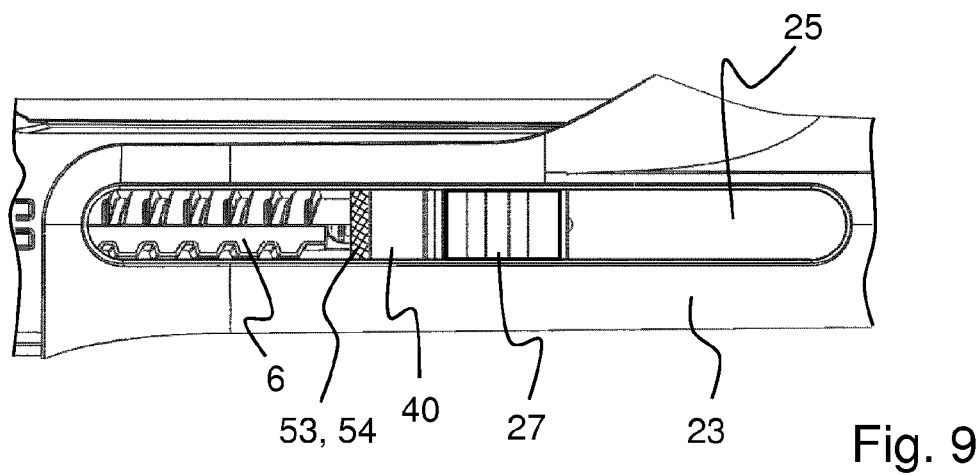
FIG. 9 shows the portion of FIG. 8 at the beginning of dose dispense in a side view.

If an axial compressive load e.g. during dose dispense is applied to the cartridge bung load indicator 40 via the piston rod 6, the coil spring 43 is compressed and the overall axial length of the cartridge bung load indicator 40 is reduced due to displacement of the first casing element 41 with regard to the second casing element. Thereby, a series of pins (or protrusions, up-stand features) 53 that are colored at their outer face 54 with a bright color and attached to the proximal end of the second casing element 42 protrude through respective apertures 55 (see FIG. 6) within the proximal end face of the first casing element 41 unmasking the pins 52. Thus, it is visually indicated to the user that the system is in a load state (see FIG. 7). This means that the load applied by the piston rod 6 to the bung 27 is greater than or equal to a predefined minimum load value. At the minimum load value the room for relative axial movement of the first casing element 41 provided by the groove 47 within the second casing element 42 and by the groove 51 of the stud 49 is used up. From this visual indication the user derives that a dispense operation is in progress. Once the axial load is removed the coil spring 43 extends again, returning the cartridge bung load indicator 40 to its "at rest" condition wherein the pins 53 no longer protrude through the apertures 55 in the first casing element 41.

Figure 5:
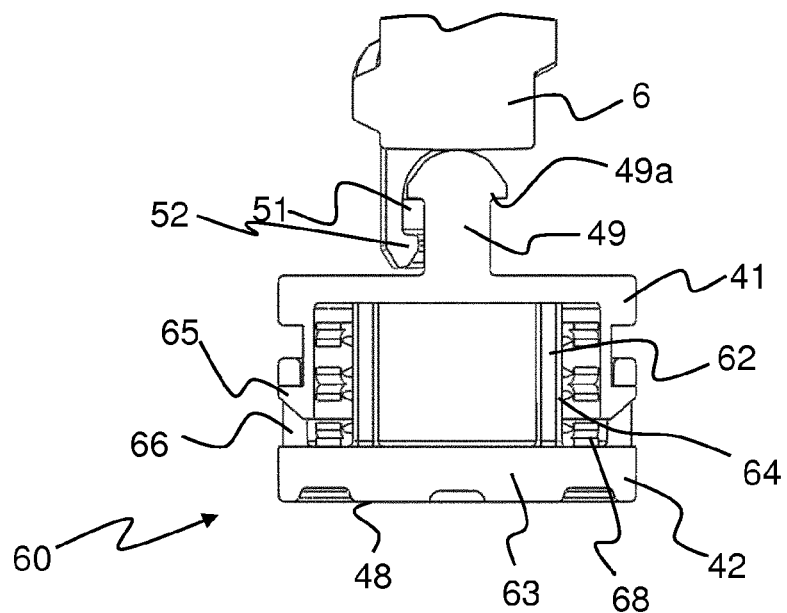
FIG. 5 shows a cross section of a second embodiment of a cartridge bung load indicator according to the disclosure.

FIG. 5 shows another embodiment of a cartridge bung load indicator 60, wherein at least one pin (protrusion, up-stand feature) 62 with a colored outer face protrudes from the distal base plate 63 of the second casing element 42 through the inner volume formed by the first and second casing elements 41, 42 in the proximal direction. Further, in contrast to the embodiment shown in FIG. 4, the first casing element 41 forms radial protrusions 65 movable within respective grooves 66 of the second casing element 42 in order to realize compressibility of the housing of the cartridge bung load indicator 60. Additionally, instead of the coil spring 43 of the embodiment shown in FIG. 4 there is a series of wave springs 68 provided as biasing means which are accommodated side by side.

As a further alternative, a colored face could be provided in another location, for example on the side wall of first casing element 41 or second casing element 42, for example on the face adjacent to protrusion 45, 65. The color could be hidden when the device is at rest, and may appear in groove 47, 66 when the system is in the load state.

Despite the constructive differences of the embodiments of the cartridge bung load indicators 40, 60 depicted in FIGS. 4 and 5 the mechanical functionality is similar and again described with reference to FIGS. 8 to 11 in the following. In these Figures the cartridge bung load indicator 40 is used, for example, but the cartridge bung load indicator 60 of FIG. 5 could be used similarly.

Prior to dose dispense and at the beginning the drug delivery device is first in an "at rest" position in which no or only a small load (lower than the predefined minimum load value) is provided by the dose mechanism 4 via the piston rod 6 to the bung 27 and the cartridge bung load indicator 40. In this state no particular visual indication is provided to the user (see FIG. 8). Subsequently, during dose dispense the load increases until the load state is reached (see FIG. 9). This state is indicated to the user by the colored flag formed by the protruding and thereby unmasked pin 53 at the proximal end of the cartridge bung load indicator 40.

Figure 10:
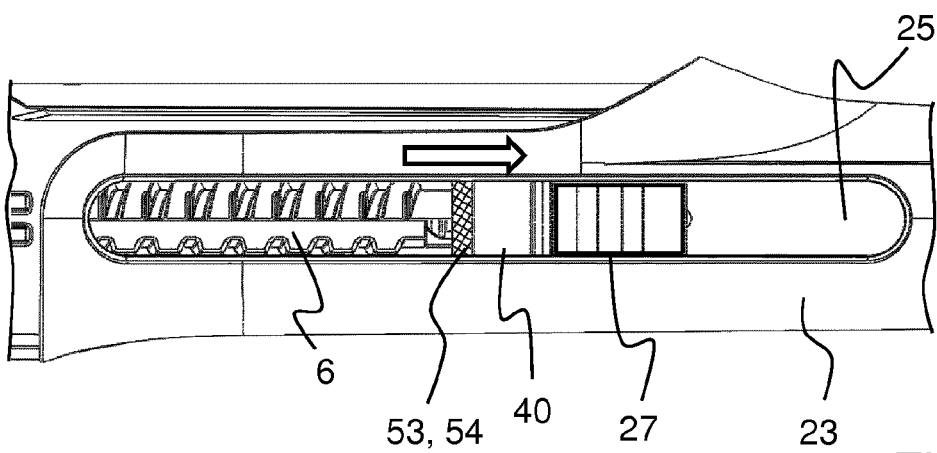
FIG. 10 shows the portion of FIG. 8 during medicament dispense in a side view.
Figure 11:
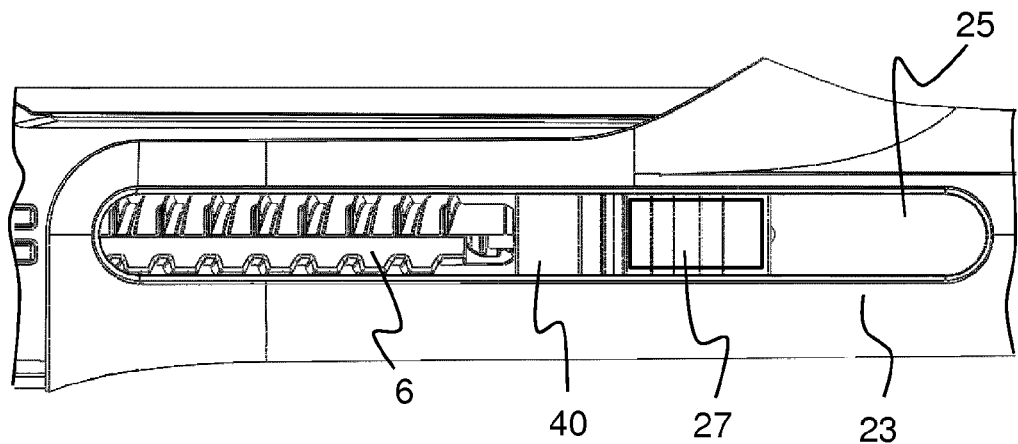
FIG. 11 depicts the portion of FIG. 8 after completion of the medicament dispense in a side view.

As the dose dispense continues (see arrow in FIG. 10) and the piston rod 6 advances during dosing, the cartridge bung load indicator 40 remains in its compressed state which is still visible as shown in FIG. 10. After the end of the axial advance of the piston rod, the spring 43 in the cartridge bung load indicator 40 extends and completes the dosing (see FIG. 11). As it does so, the colored "flag" (pin 53) disappears again showing that dose delivery is completed and that the system is relaxed, i.e. that no residual or only a small load is present in the system.

If, once initiated, the system is unable to complete the delivery of a dose (e.g. due to a blocked needle) then the cartridge bung load indicator 40 would remain in its compressed state (shown by colored indication of the load state) until corrective action was taken by the user (e.g. replace the needle with a new, unblocked one).

Figure 12:
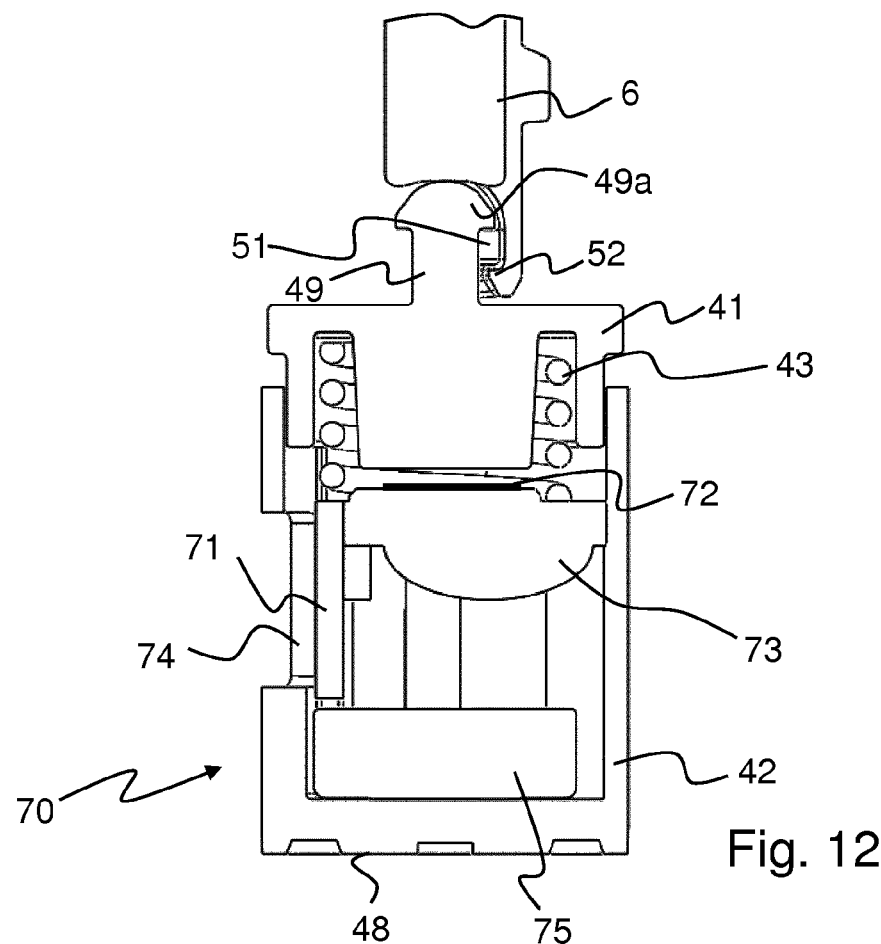
FIG. 12 depicts a third embodiment of a cartridge bung load indicator according to the disclosure in a cross section.
Figure 13:
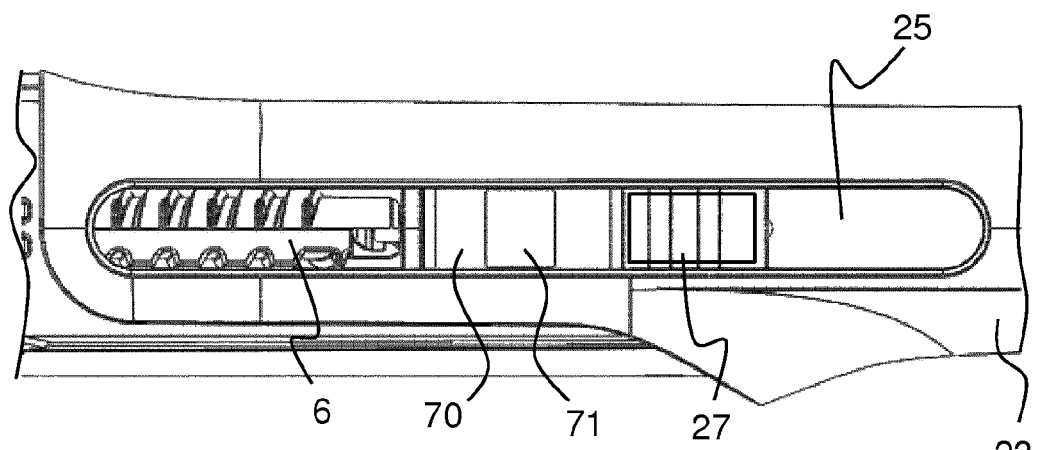
FIG. 13 shows a portion of a third embodiment of an inventive drug delivery device with a cartridge bung load indicator according to FIG. 12 in a rest position and in a side view.
Figure 14:
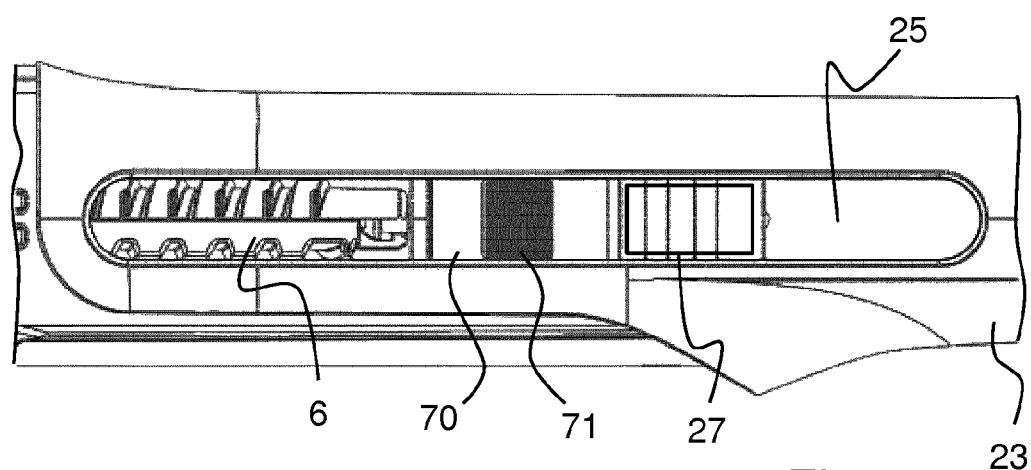
FIG. 14 depicts the portion of FIG. 13 in a load state at the beginning of medicament dispense in a side view.

As shown in FIGS. 12 to 19 and functionally identical to the above embodiments of cartridge bung load indicators 40, 60, the axial compression of the third embodiment of a cartridge bung load indicator 70 is used to activate an electronic circuit (e.g. by closing a switch or detecting a voltage at a piezo element between the first casing element 41 and the second casing element 42). The electronic circuit is used to provide a visual, tactile and/or audible indication to the user that the system is in the load state (e.g. dispense operation is in progress or needle is blocked). The visual flag may be provided by a number of means, including, but not limited to a liquid crystal display (LCD) 71 as shown in FIG. 12 and light emitting diodes (LED).

For example, if a pre-determined minimum load is exceeded a dome switch 72 is closed which is connected to a printed circuit board (PCB) 73 forming an electronic circuit comprising a processor and preferably also a memory for storage of load data. In this circuit the LCD 71 is provided for visual indication of the device's state wherein the LCD 71 is located behind a respective aperture 74 within the second housing element 42. In the load state, the LCD lights up showing a certain pre-determined color. Alternatively, the LCD may display a predefined warning symbol such as an exclamation mark or a series of symbols or pictures showing that the dose dispense is in progress. For current supply of the electronic circuit a battery 75 (e.g. a silver oxide battery) may be provided within the second casing element 42.

Figure 15:
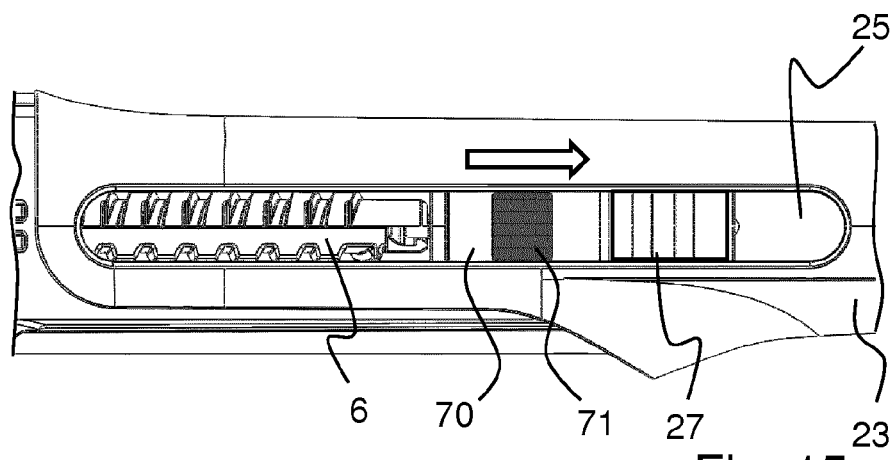
FIG. 15 illustrates the portion of FIG. 13 during dose dispense in a side view.
Figure 16:
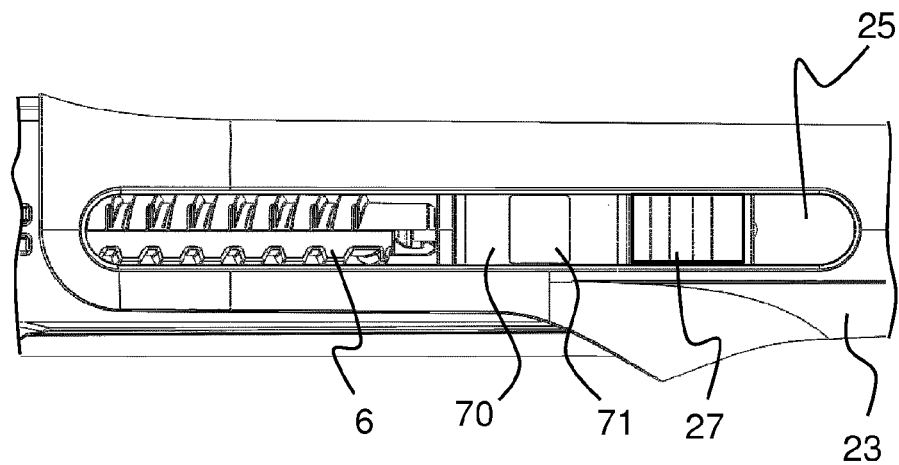
FIG. 16 shows the portion of FIG. 13 after completion of dose dispense in a side view.
Figure 17:
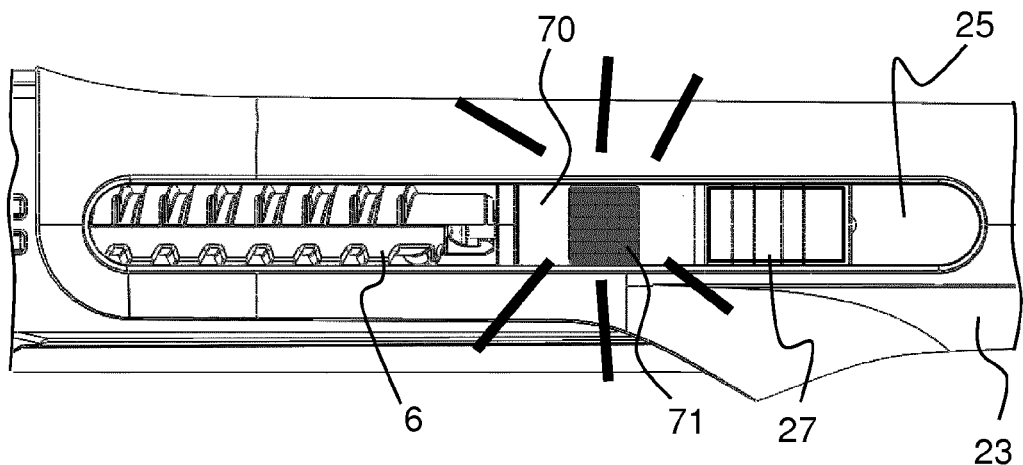
FIG. 17 depicts the drug delivery device of FIG. 13 in a load state after a predetermined time in a side view.

FIGS. 13 to 16 depict the sequence during dose dispense for the electronic version of a cartridge bung load indicator 70 shown in FIG. 12. In an "at rest" position the LCD does not light (see FIG. 13). When a certain load is applied during dose dispense the LCD lights up caused by closing the dome switch 72 thereby activating the electronics of the PCB 73 (see FIG. 14). The LCD 71 displays a predefined colored area. As the piston rod 6 advances during dosing (see arrow in FIG. 15), the cartridge bung load indicator 70 remains in its compressed state still indicating the load state as shown in FIG. 15. After the end of the axial advance of the piston rod 6, the spring 43 in the cartridge bung load indicator extends, thereby opening the dome switch 72 again and deactivating the electronic circuit. Accordingly, the illumination of the LCD 71 vanishes (see FIG. 16) or the color changes and/or the LCD 71 does not show any warning message or a different message indicating that the dose dispense is completed.

Additionally or alternatively, the electronic system could be configured to include a sound element for providing audible feedback to the user or a vibrating element providing tactile response.

If, the cartridge bung load indicator remains in a compressed state beyond a pre-determined time (e.g. 10 seconds) the LCD may be configured to flash (see FIG. 17) or display a different warning message and/or color indicating that the dispense may be blocked and cannot be completed (e.g. caused by a blocked needle) until either the blockage is removed or a further pre-defined amount of time has lapsed (for example in order to preserve battery life).

LIST OF REFERENCE NUMBERS 1 drug delivery device
2 cartridge retaining part
3 cap
4 dosing mechanism
6 piston rod
8 thread
12 dial grip
14 window or lens
16 dose scale arrangement
17 dose button
19 distal end of drug delivery device
23 cartridge holder
25 cartridge
27 bung
33 proximal end of the cartridge
35 longitudinal axis of device 1
40 cartridge bung load indicator
41 first casing element
42 second casing element
43 coil spring
45 radial protrusion
47 groove
48 end face
49 stud
49a head of stud 49
51 groove
52 rib
53 pin
54 outer face of pin
55 aperture
60 cartridge bung load indicator
62 pin
63 base plate
64 outer face of pin 62
65 protrusion
66 groove
68 wave spring
70 cartridge bung load indicator
71 LCD
72 dome switch
73 PCB
74 aperture
75 battery

The invention claimed is:

1. A drug delivery device comprising:
a piston rod which extends along a longitudinal axis of the drug delivery device;
a cartridge comprising a cartridge bung, wherein the piston rod is configured to apply an axial load in a distal direction to the cartridge bung in order to dispense a medicament contained in the cartridge; and
a cartridge bung load indicator located at a distal end of the piston rod and adapted to abut the cartridge bung, wherein the cartridge bung load indicator comprises an indicator element that visually indicates a load state of the piston rod,
wherein the cartridge bung load indicator comprises a resiliently compressible housing which decreases in length in an axial direction in response to the applied axial load, and
wherein the indicator element comprises at least one colored or patterned surface element which is uncovered in a loaded state and covered in an unloaded state.

2. The drug delivery device according to claim 1, wherein the resiliently compressible housing of the cartridge bung load indicator comprises a first casing element that is biased against a second casing element, the first and second casing elements being in slidable engagement with each other.

3. The drug delivery device according to claim 2, wherein the indicator element is disposed between a distal lace of an opening of the first casing element and a radial protrusion of the second casing element, such that the indicator element is uncovered when the first casing element and the second casing element slide relative to each other.

4. The drug delivery device according to claim 1, wherein the cartridge bung load indicator is attached to the piston rod by a connection which allows relative movement of the piston rod and the cartridge bung load indicator in the axial direction limited to a predefined distance.

5. The drug delivery device according to claim 1, wherein the drug delivery device comprises the cartridge containing the medicament and the cartridge bung located at a proximal end of the cartridge, wherein the cartridge bung load indicator abuts the bung.

6. The drug delivery device according to claim 1, wherein the resiliently compressible housing of the cartridge bung load indicator comprises a first casing element that is biased by a compression spring against a second casing element, the first and second casing elements being in slidable engagement with each other, wherein a proximal end of the compression spring engages with the first casing element and a distal end of the compression spring engages with the second casing element.

7. The drug delivery device according to claim 1, wherein the cartridge bung load indicator comprises one or more wave springs.

8. The drug delivery device according to claim 7, wherein the resiliently compressible housing of the cartridge bung load indicator comprises a first casing element that is biased by the one or more wave springs against a second casing element, the first and second casing elements being in slidable engagement with each other; wherein a proximal end of the one or more wave springs engages with the first casing element and a distal end of the one or more wave springs engages with the second casing element.

* * * * *

UNITED STATES PATENT AND TRADEMARK OFFICE
CERTIFICATE OF CORRECTION

| | | |
|---|---|---|
| PATENT NO. | : 10,675,418 B2 | Page 1 of 1 |
| APPLICATION NO. | : 15/742555 | |
| DATED | : June 9, 2020 | |
| INVENTOR(S) | : Oliver Charles Gazeley et al. | |

It is certified that error appears in the above-identified patent and that said Letters Patent is hereby corrected as shown below:

In the Specification

Column 1, Line 10, delete "in on" and insert -- on --.

In the Claims

Column 14, Line 27, Claim 3, delete "lace" and insert -- face --.

Column 14, Line 59, Claim 8, delete "other;" and insert -- other, --.

Signed and Sealed this
Twenty-eighth Day of July, 2020

Andrei Iancu
*Director of the United States Patent and Trademark Office*